United States Patent [19]
Anastassiades

[11] Patent Number: 6,133,230
[45] Date of Patent: *Oct. 17, 2000

[54] METHOD AND PHARMACEUTICAL COMPOSITION FOR CHONDROSTIMULATION WITH A PROSTAGLANDIN (E.G. MISOPROSTOL) AND TGF-β, OPTIONALLY IN COMBINATION WITH IGF-1

[75] Inventor: Tassos Anastassiades, Kingston, Canada

[73] Assignee: Queen's University at Kingston, Kingston, Canada

[*] Notice: This patent issued on a continued prosecution application filed under 37 CFR 1.53(d), and is subject to the twenty year patent term provisions of 35 U.S.C. 154(a)(2).

[21] Appl. No.: 08/860,116

[22] Filed: Jun. 19, 1997

Related U.S. Application Data

[63] Continuation of application No. PCT/CA96/00698, Oct. 23, 1996.
[60] Provisional application No. 60/005,790, Oct. 23, 1995.
[51] Int. Cl.[7] .......................... A61K 38/18; A61K 31/557
[52] U.S. Cl. .................. 514/2; 514/8; 514/530; 514/573; 514/885
[58] Field of Search .................. 514/2, 8, 530, 514/573, 885

[56] References Cited

FOREIGN PATENT DOCUMENTS

| | | |
|---|---|---|
| 434625 | 6/1991 | European Pat. Off. . |
| 445948 | 9/1991 | European Pat. Off. . |

OTHER PUBLICATIONS

Nicholson, J. Rheumatol, vol. 17, No. suppl. 20, (1990).
Dingle, J. Lipid Mediat, vol. 6, No. 1–3, (1993).
Neidel et al., Arch Orthop Trauma Surg., vol. 114, No. 1, pp. 43–48, (1994).
Brandt, Am J Med, 83:29–34, (1987).
Franceschi et al., Agents and Actions, 29:39–47, (1990).
Ohtani, Med J. Kinki Univ., vol. 18, No. 2, pp. 241–252, (1993).
Diaz, et al., Ann NY Acad Sci, 593:306–309, (1990).
Tyler, Biochem J, 260:543–548, (1989).
Morales, et al., J Biol Chem, 236:12828–12831, (1988).
Howard, et al., J Rheumatol, 20:2083–2094, (1993).
Dingle, J Rheumatol, 18(Suppl. 28):30–37, (1991).
Brandt, et al., J Clin Pharmacol, 31:673–676, (1991).
Athanassiades et al., In vitro Cell Develop Biol, 30A:510–511, (1994).
D. Heingard, et al., Methods Enzymol, 145:336–363, (1987).
Hronowski, et al., J Biol Chem, 255:9210–9217, (1980).
Hronowski, et al., Anal Biochem, 93:60–72, (1979).
Palmoski, et al., Arthritis Rheum, 23:83–91, (1980).
Muir, et al., Drugs, 35 (suppl. 1):15–23, (1988).
Slowman–Kovacs, et al., Arthritis Rheum, 26:528–531, (1989).
Kuettner, et al., J Cell Biol, 93:743–750, (1982).
Shield, Scand J Rheumatol Suppl, 92:31–52, (1992).
Sirois, et al., J Biol Chem, 267:6382–6388, (1992).
Vane, et al, Adv Prostaglandin, Thromboxane Leukot Res, 23:41–48, (1995).
Karim, Prostaglandins, 33 (Supp.):40–50, (1987).
Dingle, Adv Prostaglandin, Thromboxane and Leukot Res, 21B:955–966, (1990).
Colombo, et al., Arthritis Rheum, 26:1132–1139, (1983).
Palmoski, et al., Arthritis Rheum, 26:771–774, (1983).
Herman, et al., J Rheumatol, 13:1014–1018, (1986).
Kararli et al., Adv Exp Med Biol, 302:275–289, (1991).
Geng, et al., J Immunol, 155:796–801, (1995).
Osborn, et al., J Orthop Res, 7:35–42, (1989).
Huskisson, et al., J Rheumatol, 22:1941–1946, (1995).
T. Anastassiades et al., The Journal of Rheumatology, 1998 vol. 25(10) pp. 1962–1967.
R.L. Smith, Editorial, The Journal of Rheumatology, 1998 vol. 25(10) pp. 1871–1873.
Chopra et al., Arthritis & Rheumatsm, vol. 38, No. 9 Suppl. p. S161 1950 (Abstract), Oct. 21, 1995.
Andrews et al—Biochem. Biophys. Res. Commun. vol. 162, No. 1 pp. 144–150, Jul. 1989.

*Primary Examiner*—Frederick Krass
*Attorney, Agent, or Firm*—Fitzpatrick, Cella, Harper & Scinto

[57] ABSTRACT

A pharmaceutical composition comprising a prostaglandin such as misoprostol and TGF-B in amounts sufficient to stimulate production of chondrocyte matrix is disclosed which exhibit therapeutic synergy.

11 Claims, 6 Drawing Sheets

METHOD AND PHARMACEUTICAL COMPOSITION FOR CHONDROSTIMULATION WITH A PROSTAGLANDIN (E.G. MISOPROSTOL) AND TGF-β, OPTIONALLY IN COMBINATION WITH IGF-1

This application claims the benefit of U.S. Provisional Application Ser. No. 60/005,790, filed Oct. 23, 1995, the contents of which are hereby incorporated by reference, and is a continuation of PCT/CA96/006898, filed Oct. 23, 1996.

BACKGROUND OF THE INVENTION

This invention relates to the use of certain prostaglandins in combination with certain growth factors to promote chondrocyte matrix or cartilage matrix production and thereby promote cartilage matrix synthesis and/or prevent the inhibition of cartilage matrix synthesis. In particular the invention relates to the use of a combination of prostaglandin, TGF-β and/or IGF-1 to stimulate chondrocyte matrix or cartilage matrix production and thereby promote cartilage matrix synthesis and/or prevent the inhibition of cartilage matrix synthesis.

DESCRIPTION OF RELATED ART

It has been recognized for over 2 decades that cartilage is capable of degradation and synthesis of its extracellular matrix (Dingle, J. T. "The Role of Lysosomes in Connective Tissues Disease" in Hill, A. G., ed.) *Modern Trends in Rheumatology*, pp. 110–120, Butterworths 1966.) It is now recognized that repair of cartilage damage is possible. (Nakata, et al. "The Injury and Repair of Human Articular Cartilage: A Morphological Study of 192 Cases of Osteoarthritis" *J. Japan. Orthop. Ass.* 1986, 60, 763–775.) In view of the recognition that cartilage damage, including damage to the cartilage matrix, as well as the repair of such cartilage damage may be controllable, it would be desirable to find compounds which could be administered as pharmaceutical agents (medicaments) for the treatment of patients susceptible to or exhibiting cartilage damage or inhibition of cartilage synthesis to inhibit such cartilage damage and/or enhance the repair of cartilage damage by overcoming the inhibition of cartilage matrix synthesis.

Non Steroidal Anti-Inflammatory Drugs ("NSAID") have long been used for the treatment of osteoarthritis ("OA") and rheumatoid arthritis ("RA") to provide relief from the pain associated with such diseases and to increase the range of movement in the patients with such diseases. It has been found that some NSAIDs can inhibit cartilage matrix synthesis or promote cartilage damage. Thus, not only can cartilage damage arise due to such conditions as RA or OA, but also the pharmaceuticals indicated for treatment of such OA and RA can also exhibit certain cartilage damaging properties.

It has been known for many years that articular cartilage chondrocytes retain their ability to synthesize matrix components throughout life and exhibit the ability to take up sulphate and form new glycosaminoglycans ("GAGs"). GAGs are important components of proteoglycans which are in turn key constituents of cartilage matrix. It would be desirable to identify compounds which can be used as a pharmaceutical product to enhance and/or promote the synthesis and repair of cartilage in a subject having damaged cartilage or otherwise in need of protection from cartilage degeneration.

It has been found that the catabolic action of the cytokine interleukin-1, ("IL-1" or "hrIL1α") plays an important role in inflammatory diseases and a role in cartilage damage and degeneration. Suppression of IL-1 production is possible using exogenous prostaglandin E (Bodger, et al. "Immuno Modulatory Approaches To The Treatment of Inflammation" in (Johns, W. F. ed.) *Section I; Endocrinology, Immunology and Metabolic Disorders* Annual Reports in Medicinal Chemistry, 1988, pp. 171–180 Academic Press Inc.; Kunkel, et al. "Arachidonic Acid Metabolites Regulate Interleukin 1 Production" *Biochem. BioPhys. Res. Commun.* 1985, 128, 892–897; and Numo, et al. "Present Status and New Prospectives in Non Steroidal Anti-Inflammatory Drug Therapy" *Scand. J. Rheumatol.* 1987, Supplement 66, 75–83.) In view of the role of IL-1 in cartilage degeneration it is highly desirable to find a compound which could diminish the negative effects of IL-1 on cartilage matrix.

As is demonstrated herein, NSAID-induced inhibition of prostaglandin synthesis in mammalian chondrocytes can be suppressed by administration of a combination of certain prostaglandins, in particular misoprostol, with growth factors TGF-β and/or IGF-I. Moreover, the combination is shown to have a chondrostimulatory effect, promoting proteoglycan synthesis.

This invention therefore is directed to the use of certain prostaglandins in combination with growth factors to prevent cartilage matrix damage or cartilage matrix synthesis inhibition and to promote cartilage matrix synthesis in a patient susceptible to such cartilage matrix damage and such cartilage matrix synthesis inhibition.

SUMMARY OF THE INVENTION

This invention provides a pharmaceutical composition comprising a prostaglandin having the structure:

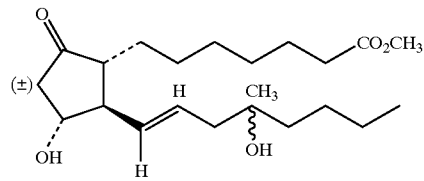

and a compound chosen from the group consisting of TGF-β and IGF-1 wherein the prostaglandin, TGF-β and IGF-1 are present in an amount effective to promote the production of chondrocyte matrix or prevent the degeneration of chondrocyte matrix. The invention also provides a method of stimulating the production of, or preventing the degeneration of, cartilage matrix in a subject in need thereof.

DETAILED DESCRIPTION OF THE INVENTION

Figure 1:
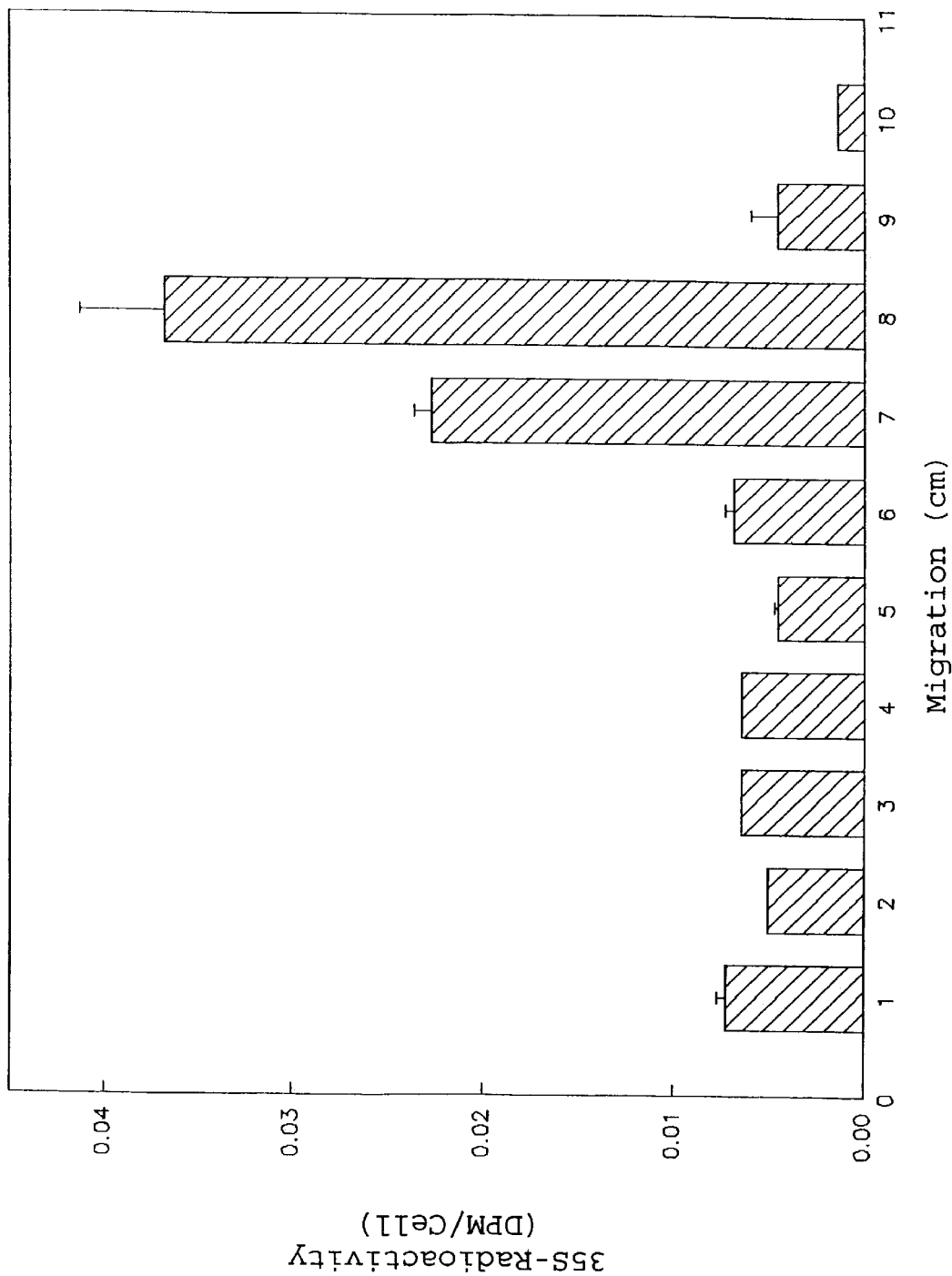
FIG. 1 shows a typical profile for the cellulose acetate electrophoresis of radiolabelled GAG. Each bar represents average of six values of $^{35}$S-radioactivity determined at a given distance from the origin for GAG samples isolated from the media of a duplicate set of cultures. The error bars represent standard deviation.

The invention provides a pharmaceutical composition comprising a prostaglandin having the structure

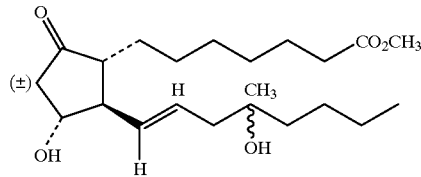

and a compound chosen from the group consisting of TGF-β and IGF-1 wherein the prostaglandin, TGF-β and IGF-1 are present in an amount effective to promote the production of chondrocyte matrix or prevent the degeneration of chondrocyte matrix. For the purposes of this invention the terms "chondrocyte matrix" and "cartilage matrix" are used interchangeably. In one embodiment, the pharmaceutical composition comprises a prostaglandin and TGF-β. In a separate embodiment, the pharmaceutical composition comprises a prostaglandin, TGF-β and IGF-1. The pharmaceutical composition can be used to stimulate production of the chondrocyte matrix and thereby promote cartilage matrix synthesis or inhibit cartilage matrix degeneration in a subject susceptible to cartilage matrix degeneration or cartilage matrix synthesis inhibition.

The invention also provides a method of treating a subject which comprises administering a pharmaceutical composition comprising a prostaglandin having the structure:

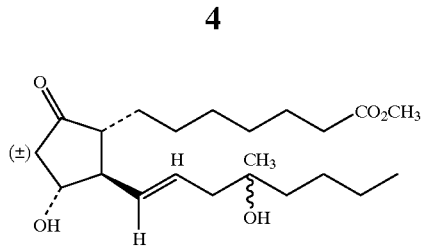

and a compound chosen from the group consisting of TGF-β and IGF-1 wherein the prostaglandin, TGF-β and IGF-1 are present in an amount effective to promote the production of chondrocyte matrix. In one embodiment, the method comprises administration of a pharmaceutical composition which comprises a prostaglandin and TGF-β. In a separate embodiment, the method comprises administration of a pharmaceutical composition which comprises a prostaglandin, TGF-β and IGF-1.

Subjects to which the pharmaceutical compositions of this invention would be administered include all vertebrates, in particular mammals. In a preferred embodiment the subject would be human. The methods of this invention are practiced by administering to a subject having damaged cartilage or otherwise in need of protection from cartilage degeneration an effective chondrocyte matrix growth-stimulating amount of one of the pharmaceutical compositions described above. In addition, the method can be practice by co-administration of the compounds which form the above-described pharmaceutical compositions in combination, each in the form of a separate pharmaceutical composition.

The prostaglandin compounds, and their preparation are described in U.S. Pat. Nos. 3,965,143 and 4,060,691. The prostaglandin compounds herein are commercially available under the USAN (United States Adopted Name) misoprostol as a pharmaceutical which has been accepted for use in the treatment of NSAID induced gastric and gastrointestinal ulcers in many countries, including the United States, and which is commercially available by prescription in such countries. Misoprostol, ((+/−)-methyl-11α, 16-dihydroxy-16-methyl-9-oxoprost-13E-en-1-oate) is a synthetic analog of prostaglandin $E_1$ ($PGE_1$) and is sold by G. D. Searle & Co. (Chicago, Ill.) under the name CYTOTEC. Examples of nonsteroidal anti-inflammatory drugs include, but are not limited to, aspirin, ibuprofen and naproxen. NSAIDs are known to contribute to degradation of articular cartilage and/or articular cartilage matrix.

Transforming growth factor-s (TGF-β) is a multipotent dimeric polypeptide growth factor that functions as an inducer during vertebrate development. Depending on target cell type, TGF-β may function as a growth inhibitor or as a growth stimulator. It belongs to a protein superfamily whose members share structural, and presumably functional, features. TGF-β is reviewed in Massagui, *Ann. Rev. Cell Biol.*, Vol. 6, page 597 (1990), the disclosure of which is hereby incorporated by reference.) Virtually all mammalian cells have TGF-β receptors that control a variety of functions depending on cell lineage.

Insulin-like growth factor-I (IGF-I) is a polypeptide growth factor belonging to the diverse insulin protein super-family (Blundell and Humbel, *Nature*, Vol. 287, pages 781–787, the disclosure of which is hereby incorporated by reference. Like insulin, IGF-I binds to a cell surface receptor tyrosine kinase, albeit a different receptor than the insulin receptor.

The following patents are incorporated by reference into this specification to more completely describe the invention: U.S. Pat. No. 5,324,639 (Brierley et al.) (teaches recombinant techniques for the production of IGF-1); U.S. Pat. No. 4,886,747 (Derynck et al.) (teaches recombinant techniques for the production of TGF-β); U.S. Pat. No. 5,210,074 (Nakanishi et al.) (teaches a method for preparing a dried composition of IGF-1); U.S. Pat. No. 4,983,581 (Antoniades et al.) (teaches the preparation of pharmaceutical compositions containing TGF-β and IGF-1); U.S. Pat. No. 4,929,442 (Powell) (teaches the preparation of pharmaceutical compositions containing TGF-β); U.S. Pat. No. 5,444,045 (Francis et al.) and U.S. Pat. No. 5,168,102 (Cogburn) (teach the administration of compositions comprising IGF-1 to birds); U.S. Pat. No. 5,444,047 (DiPasquale) (teaches the therapeutic application of IGF-1).

By virtue of the activity of the compounds described herein in stimulating chondrocyte matrix production, and thereby promoting cartilage growth or inhibiting cartilage damage, the compounds are useful in inhibiting cartilage damage which may arise as a result of a natural condition such as osteoarthritis or rheumatoid arthritis or a provoked condition such as can occur by administration of NSAID therapy. A physician or veterinarian of ordinary skill can determine whether a subject exhibits or is susceptible to articular degeneration and associated cartilage damage.

The compounds can be administered in such oral dosage forms as tablets, capsules, soft gels, pills, powders, granules, elixirs, or syrups. The compounds can also be administered intravascularly, intraperitoneally, subcutaneously, intramuscularly, intraarticularly, or topically, using forms known to the pharmaceutical art. Moreover, they can be administered rectally or vaginally, in such forms as suppositories or bougies.

For the orally administered pharmaceutical compositions, the prostaglandin will typically be administered in a mixture with suitable pharmaceutical diluents, excipients, or carriers (collectively referred to herein as "carrier" materials) suitably selected with respect to the intended form of administration. That is, oral tablets, capsules, soft gels, elixirs, syrups, drops and the like, and consistent with conventional pharmaceutical practices.

For example, for oral administration in the form of tablets or capsules, a therapeutically effective amount of one or more compounds of the present invention can be combined with any oral non-toxic pharmaceutically acceptable inert carrier such as lactose, starch, sucrose, cellulose, magnesium stearate, dicalcium phosphate, calcium phosphate, mannitol, and the like, or various combinations thereof.

For oral administration in liquid forms, such soft gels, elixirs, syrups, drops and the like, a therapeutically effective amount of an active combination of prostaglandin, TGF-β and IGF-1 can be combined with any oral non-toxic pharmaceutically acceptable inert carrier such as water, saline, ethanol, polyethylene glycol, propylene glycol, corn oil, cottonseed oil, peanut oil, sesame oil, benzyl alcohol, various buffers, and the like, or various combinations thereof. Moreover, when desired or necessary, suitable binders, lubricants, disintegrating agents, and grilling agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes, or combinations thereof. Lubricants for use in these dosage forms include boric acid, sodium benzoate, sodium acetate, sodium chloride, and the like, or combinations thereof. Disintegrators include, without limitation, starch, methylcellulose, agar, bentonite, agar gum, and the like, or combinations thereof. sweetening and flavoring agents and preservatives can also be included where appropriate. In the practice of this invention, oral administration would require the use of carriers or other components in the pharmaceutical composition which would protect the growth factors from digestion in a subject's gastrointestinal tract.

For intravascular, intraarticular, intraperitoneal, subcutaneous, or intramuscular administration, one or more compounds of the present invention can be combined with a suitable carrier such as water, saline, aqueous dextrose, and the like. It is also anticipated that the claimed pharmceutical compositions could be formulated for topical administration, wherein therapeutically effective amounts of one or more the compounds can be combined with pharmaceutically acceptable creams, oil, waxes, gels, including oil-based and water-based gels, and the like.

Regardless of the route of administration selected, the prostaglandins herein are formulated in a pharmaceutically acceptable dosage form by conventional methods known to those skilled in the art.

Regardless of the route of administration selected, a non-toxic therapeutically effective quantity of one or more compounds is employed in the treatment. The dosage regimen for stimulating chondrocyte matrix production and thereby preventing inhibition of cartilage synthesis or inhibiting cartilage damage is selected in accordance with a variety of factors, including the type, age, weight, sex, and medical condition of the subject, the severity of the cartilage damage, the route of administration, and the particular composition, including the biological activity of the compounds in the composition, employed in the therapeutic regimen. A physician or veterinarian of ordinary skill can readily determine and prescribe the effective amount of the drug required to prevent or arrest the progress of the condition. In so proceeding, the physician or veterinarian can employ relatively low doses at first and subsequently increase the dose until a maximum response is obtained.

The compounds herein can be combined with a variety of pharmaceutically acceptable carriers and administered in a variety of dosage forms such as pills, tablets and pre-formulated liquids as well as sustained dosage forms.

A particularly preferred stable solid dosage form of the compound (+/−) methyl 11α,16-dihydroxy-16-methyl-9-ozoprost-13E-en-1-oate is a stabilized formulation as disclosed in U.S. Pat. No. 4,301,146. The formulation disclosed in the patent is the commercially available stabilized formulation for misoprostol. The commercially available misoprostol is stabilized with hydroxypropylmethylcellulose (HPMC) as set forth in the patent. For the purposes of the use of misoprostol, the commercially available misoprostol is acceptable for use in the invention herein.

The following example is provided to further illustrate the invention. It is not intended, and should not be interpreted, to limit the scope of the invention which is defined in the claims which follow thereafter.

EXAMPLE 1

Materials. ASA and $^{35}$S-sulfate were obtained from ICN (Costa Mesa, Calif.). Misoprostol was provided by Searle (Skokie, Ill.). Porcine platelet TGF-β (referred to hereafter as TGF-β) and human recombinant IGF-1 were from R and D Systems. CMRL-1969 medium was from Connaught Laboratories (Willowdale, Ontario, Canada). Penicillin-streptomycin and fetal bovine serum (FBS) were obtained from Gibco. Cetylpyridinium chloride (CPC), chondroitin sulfate, hyaluronic acid and papain were from Sigma Chemical Co (St. Louis, Mo.).

Isolation and Culture of Chondrocytes. Chondrocytes were released by collagenase digestion from minces of BAC obtained aseptically from the ankle joints of 1–2 year old bovines within 2–4 hours of slaughter, by the method described in Howard, S., Anastassiades, T. P., *J. Rheumatol.*, (1993) Vol. 20, pages 2083–2094; and Anthanassiades A., Anastassiades, T. P. *In vitro Cell Develop. Biol.*, (1994) Vol. 30A, pages 510–511. The released cells were suspended in CMRL-1969 medium containing 20% FBS and 2% penicillin-streptomycin (growth medium) and seeded into 6-well (35 mm diameter) culture plates (Falcon) containing 2 ml of growth medium to achieve a final density of 300,000–500,000 cells/well. The cells were grown to confluence with refeeding every alternate day with the growth medium. At confluence, the FBS concentration in the medium was stepped-down gradually to 5% by first replacing the growth medium with CMRL-1969 medium containing 10% FBS and 2% penicillin-streptomycin, allowing the cells to adapt for 2 days, and then replacing the latter medium with CMRL-1969 medium containing 5% FBS and 2% penicillin-streptomycin (incubation medium).

Treatment and Radiolabelling of Cultures. After allowing the cultures to adapt for 2 days in the incubation medium, the medium was removed and replaced with 2 ml of fresh incubation medium. Following addition of various test agents, dissolved in appropriate solvents, separately and in different combinations, to triplicate sets of culture wells, the cultures were pre-incubated for 2 days. ASA, misoprostol and TGF-β were dissolved in distilled water, absolute ethanol and 4 mM HCl/1mg/ml BSA, respectively, and added to the culture wells in appropriate, small volumes to give final concentrations of 10 ng/ml TGF-β, 250 µg/ml ASA and 80 ng/ml misoprostol. IGF-1 was dissolved directly in the incubation medium prior to its addition to the cultures. Equivalent volumes of ethanol and 4 mM HCl/1mg/ml BSA were added to control cultures and to cultures lacking either solvent addition. The polypeptide growth factors were added at optimal concentrations for the stimulation of GAG synthesis in the BAC system. The optimal stimulatory concentration for TGF-β was 10 ng/ml (as reported in Howard, S. et al. *J. Rheumatol.*, (1993) above) and for IGF-1 it was 150 ng/ml (personal observations).

After pre-incubation, the media containing the test agents were removed from the cultures and replaced with fresh incubation medium and the appropriate test agents at the same concentrations as during pre-incubation. $^{35}$S-sulfate was then added to all culture wells to achieve a final concentration of 10 µCi/ml and the cultures incubated for 2 more days. In these experiments a stabilizer for misoprostol, such as hydroxypropylmethyl cellulose (HPMC) noted above was not added to the cultures.

Cell Counting. At the end of incubation, the radiolabelled incubation medium was removed and stored at −20° C., the cells rinsed with phosphate buffered saline (PBS) and detached by incubation with 0.25% trypsin at 37° C. Trypsinization was terminated by adding the growth medium, containing 20% FBS, and the cells counted on a Coulter counter, after dilution of the released cells in Hematall isotonic diluent.

Determination of 35-S Incorporation into GAG. After supplementing the culture medium with hyaluronic acid and chondroitin sulfate as the carrier GAGs, the newly synthesized, radiolabelled GAG were isolated by digestion of protein core of the peptidoglycans with papain followed by precipitation of the released GAG with CPC and ethanol using the method described in Hronowski, L., Anastassiades, T. P., *J. Biol. Chem.*, (1980) Vol. 255, pages 9210–9217. The final GAG precipitate was dissolved in 200 µl of distilled water and an aliquot electrophoresed on a cellulose acetate strip using the method described in Hronowski, L., Anastassiades, T. P., *Anal. Biochem.*, (1979) Vol. 93, pages 60–72. After staining, destaining and drying of the electrophoresed strip, the strip was cut into 1 cm sections and the radioactivity in each section determined by scintillation counting in Betamax (ICN).

A typical electrophoretic profile of the isolated, radiolabelled GAG is shown in FIG. 1. Virtually all of the radioactivity incorporated from $^{35}$S-sulfate into the GAGs precipitated by CPC and subjected to electrophoresis was identified as chondroitin sulfate by digestion with the specific chondroitinases ABC and AC using the method described in Howard, S. et al. *J. Rheumatol.*, (1993), and Hronoski et al. *Anal. Biochem.*, (1979) above. Hereafter, the incorporated $^{35}$S -radioactivity co-migrating with carrier chondroitin sulfate (generally bands number 7 and 8, as shown in FIG. 1) will be designated to reflect net synthesis of the sulfated GAG, accumulating into the culture medium over the 2 day period of radio labelling of the BAC cultures (FIGS. 2–6).

RESULTS. The BAC system is particularly suitable for assessing effects of growth factors and drugs since it does not present a tissue permeability problem for these substances and has better reproducibility among replicate cultures than the slice or organ culture systems. See, Anthanassiades A., et al., In vitro Cell Develop. Biol., (1994) above.

Figure 2:
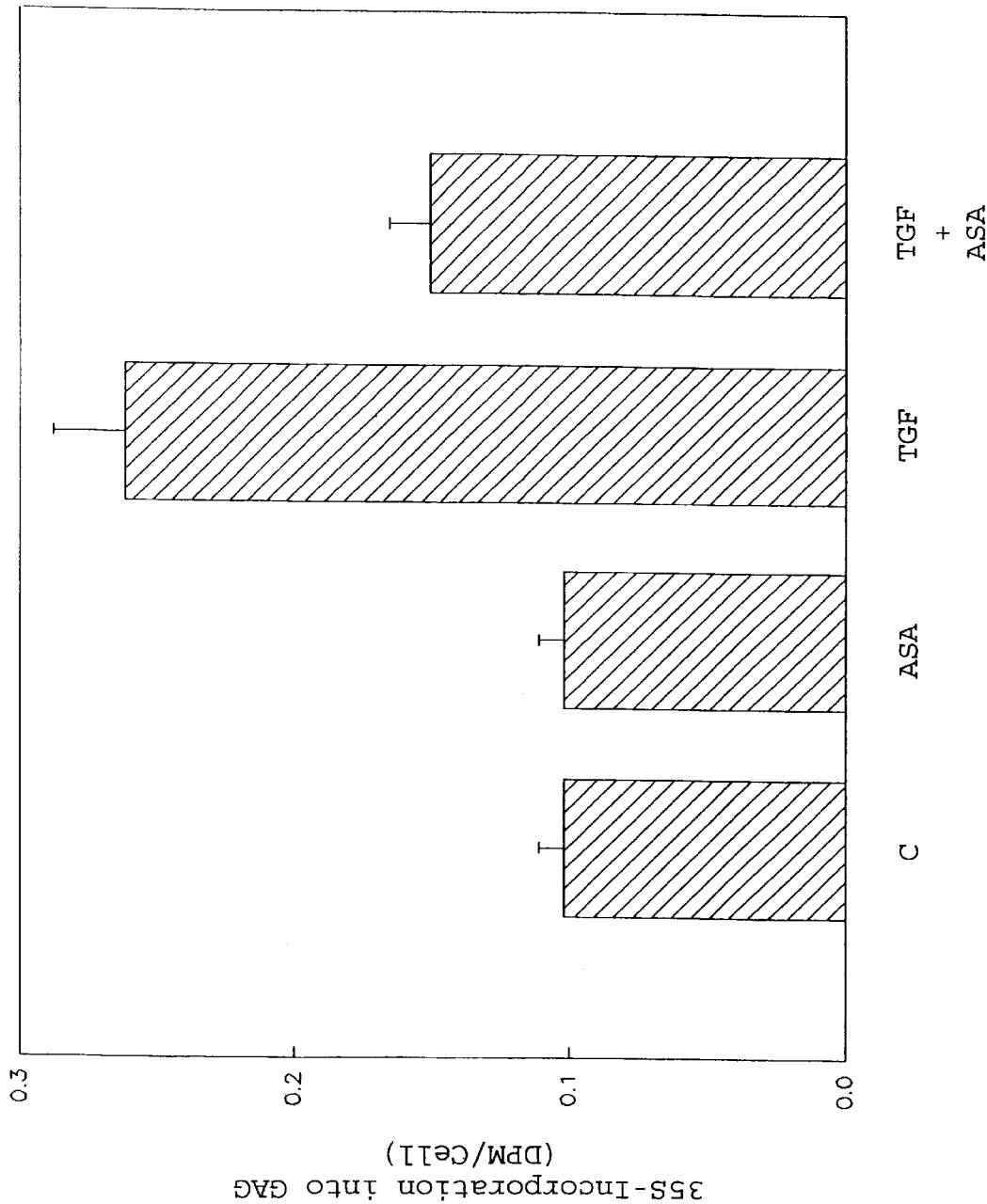
FIG. 2 shows the effects of acetylsalicylic acid ("ASA") on the basal and TGF-β-stimulated synthesis of GAG by bovine articular chondrocytes ("BAC") cultures: "C" represents control cultures with no treatment; "ASA" represents cultures treated with 250 μg/ml ASA; "TGF" represents cultures treated with 10 ng/ml TGF-β; "ASA+TGF" represents cultures treated with both 250 μg/ml ASA and 10 ng/ml TGF-β. Each bar represents average value of six determinations of $^{35}$S-incorporation into GAG for GAG samples isolated from media of a duplicate set of cultures. The error bars represent standard deviation.
Figure 3:
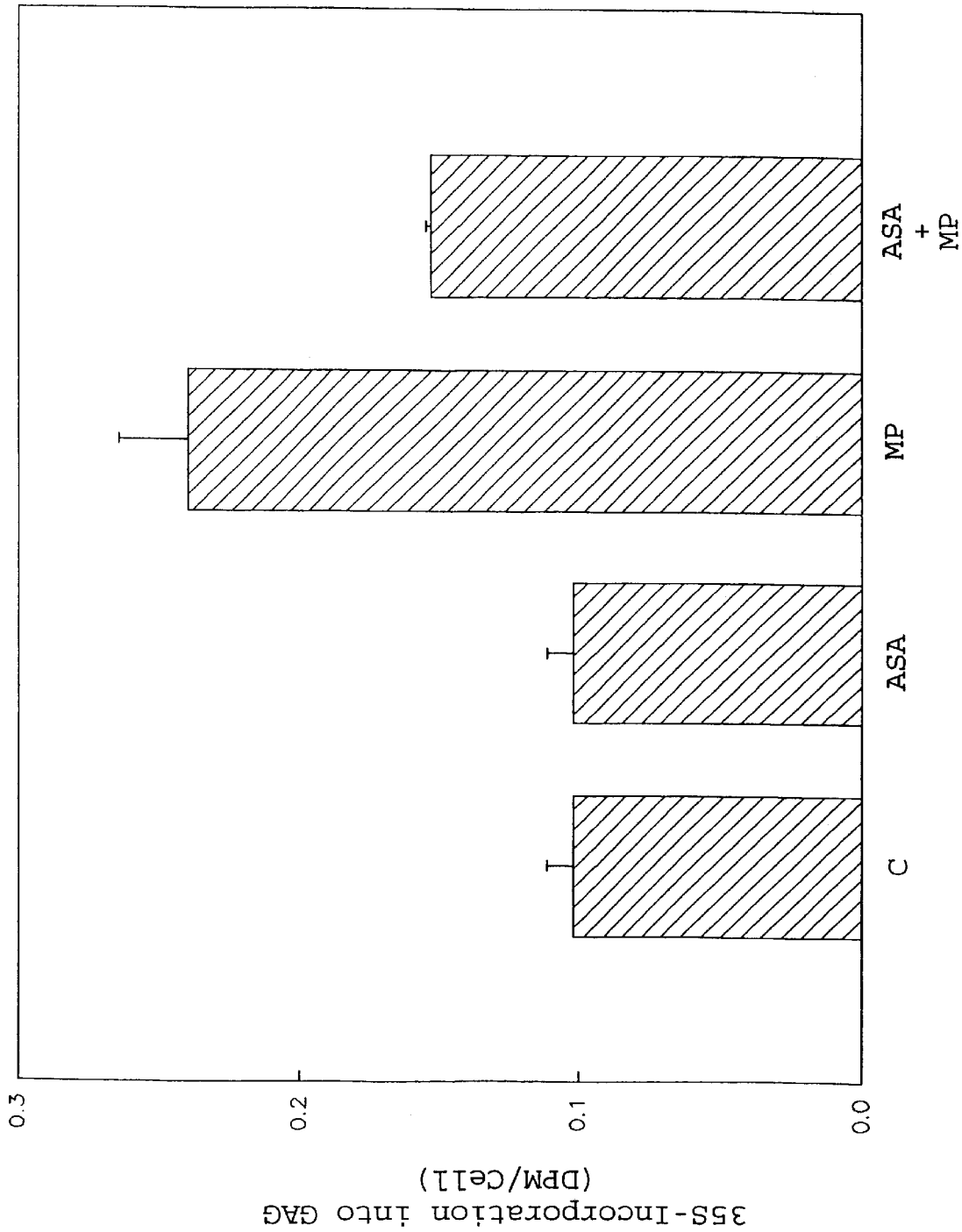
FIG. 3 shows the effects of ASA and misoprostol, separately and in combination, on GAG synthesis by BAC cultures. "C" represents control cultures without any treatment: "ASA" represents cultures treated with 250 μg/ml ASA; "MP" represents cultures treated with 80 ng/ml misoprostol; "ASA+MP" represents cultures treated with both 250 μg/ml ASA and 80 ng/ml misoprostol.
Figure 4:
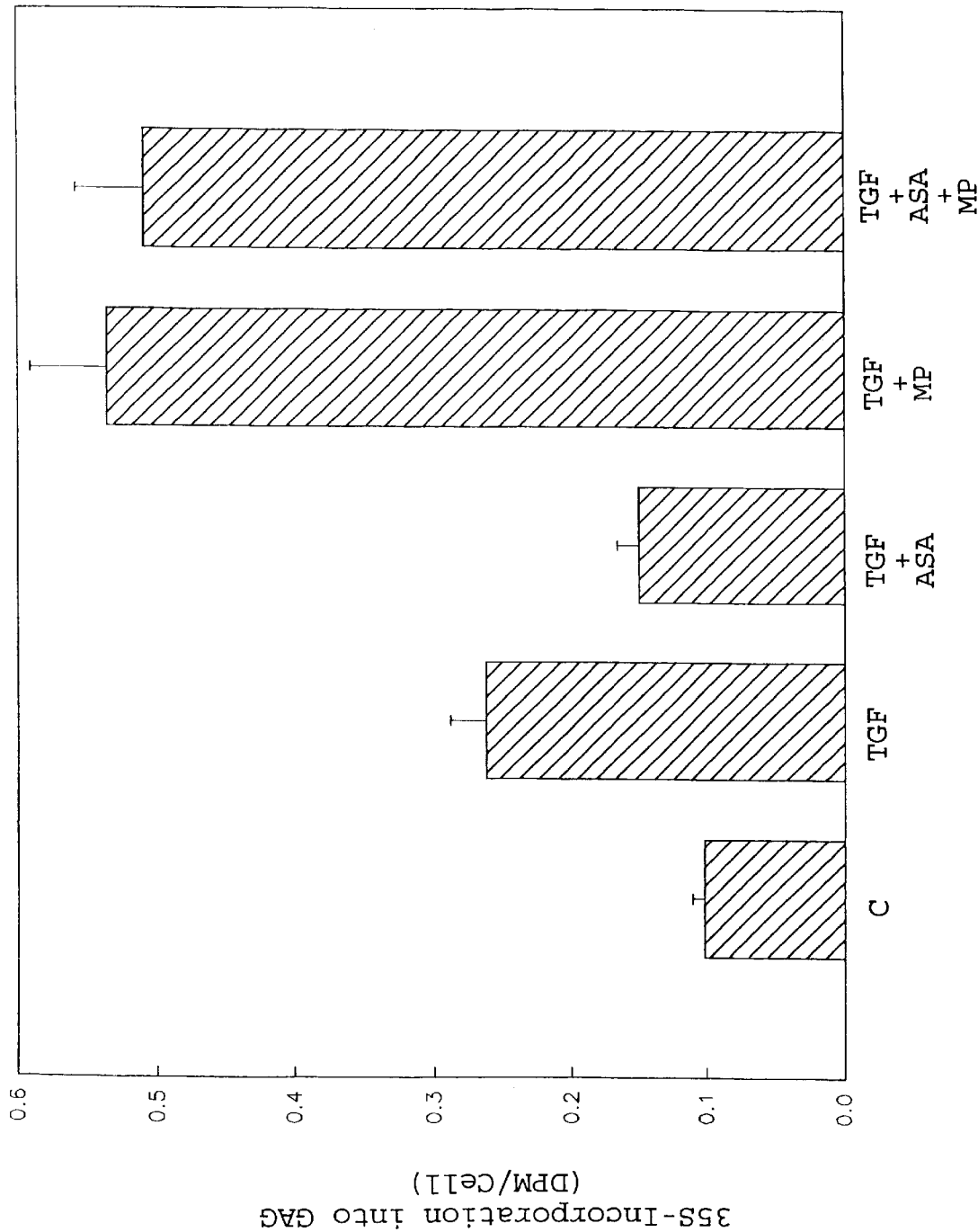
FIG. 4 shows the effects of TGF-β, ASA and misoprostol, separately and in various combinations, on GAG synthesis by BAC cultures. "C" represents control cultures; "TGF" represents cultures treated with 10 ng/ml TGF-β; "ITGF+ASA" represents cultures treated with 10 ng/ml TGF-β and 250 μg/ml ASA; "TGF+MP" represents cultures treated with 10 ng/ml TGF-β and 80 ng/ml misoprostol; "TGF+ASA+MP" represents cultures treated with 10 ng/ml TGF-β, 250 μg/ml ASA and 80 ng/ml misoprostol simultaneously.

Addition of ASA (250 µg/ml ) alone to BAC cultures had no significant effect on basal GAG synthesis (FIG. 2). While the addition of TGF-β (10 ng/ml) alone stimulated GAG synthesis by 158%, addition of TGF-β together with ASA suppressed this stimulation to 48% above the control value (FIG. 2). The addition of misoprostol (80 ng/ml) alone to the cultures caused 135% stimulation of GAG synthesis, whereas addition of misoprostol in combination with ASA reduced the misoprostol-induced stimulation of GAG synthesis to 49% (FIG. 3). The addition of misoprostol in combination with TGF-β showed 142% greater stimulation of GAG synthesis than the sum of the stimulatory effects observed with misoprostol and TGF-β separately (FIG. 4). Also, addition of misoprostol together with TGF-β almost completely abolished the suppressive effects of ASA on the stimulation of GAG synthesis by either misoprostol or TGF-β alone.

Figure 5:
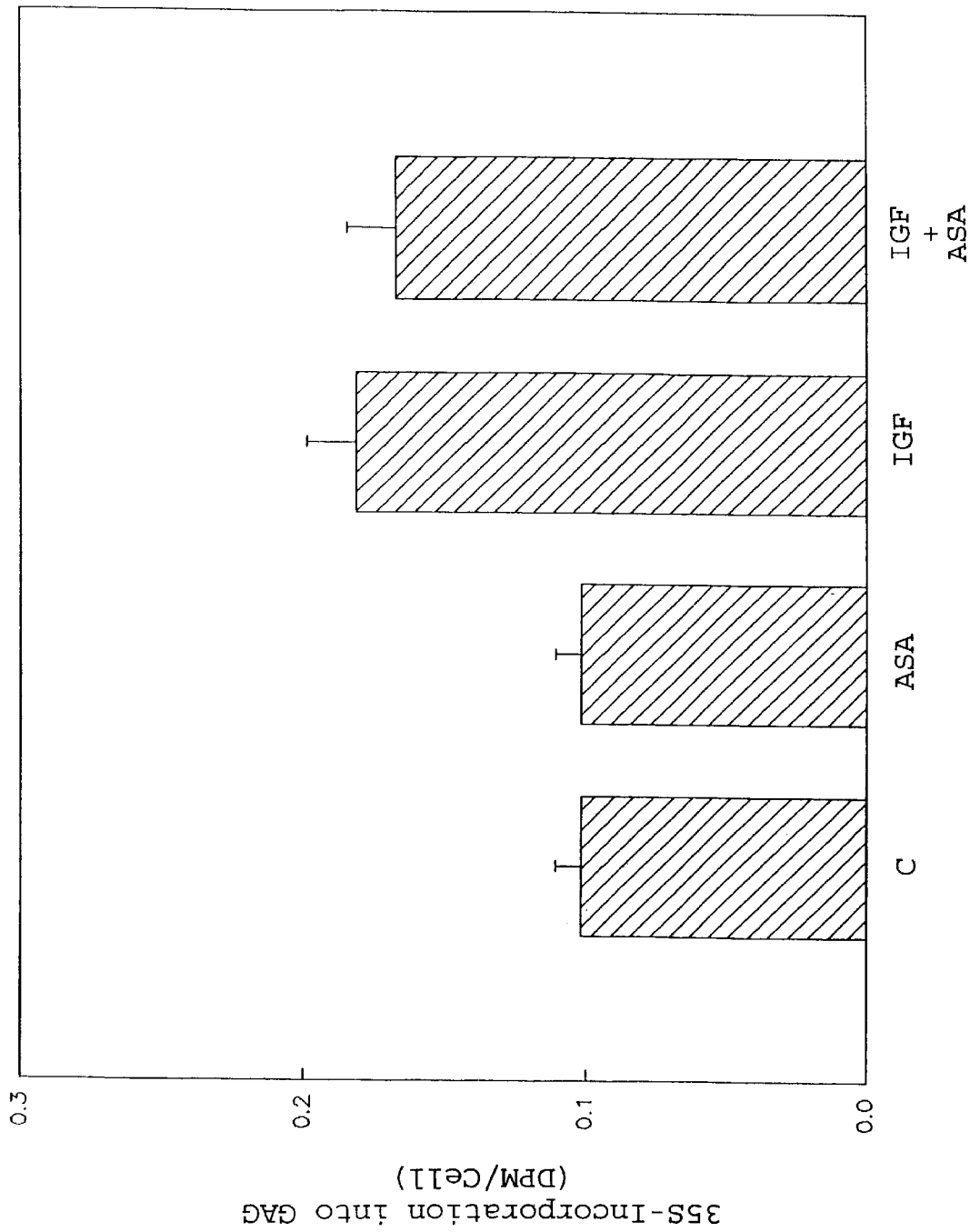
FIG. 5 shows the effects of ASA on basal and IGF-I-stimulated GAG synthesis by BAC cultures. "C" represents control cultures; "ASA" represents cultures treated with 250 μg/ml ASA; "IGF" represents cultures treated with 150 ng/ml IGF-1; "ASA+IGF" represents cultures treated with both 250 μg/ml ASA and 150 ng/ml IGF-1.
Figure 6:
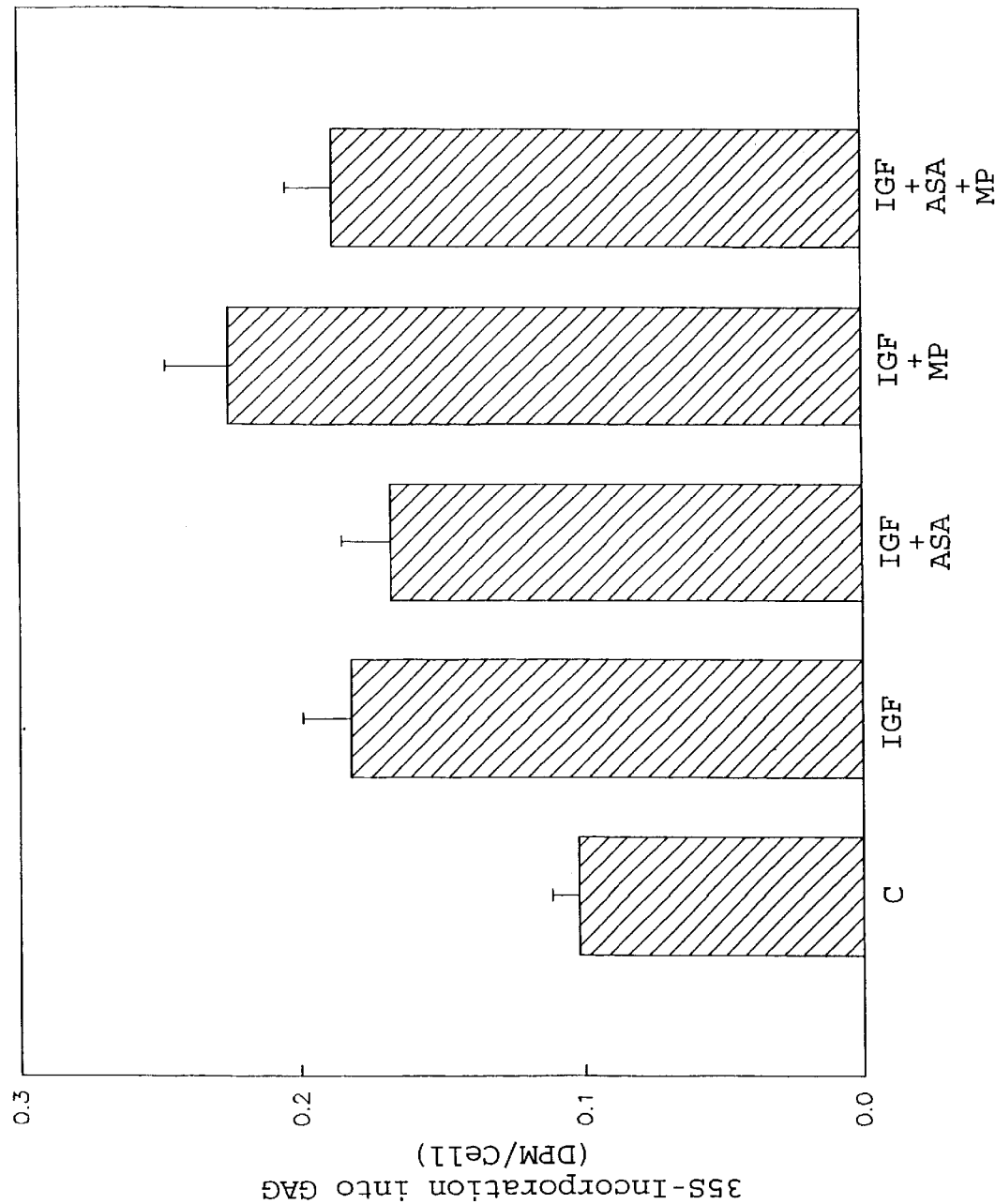
FIG. 6 shows the effects of IGF-1, ASA and misoprostol, separately and in various combinations, on GAG synthesis by BAC cultures. "C" represents control cultures; "IGF" represents cultures treated with 150 ng/ml IGF-1; "IGF+ASA" represents cultures treated with 150 ng/ml IGF-1 and 250 μg/ml ASA; "IGF+MP" represents cultures treated with 150 ng/ml IGF-1 and 80 ng/ml misoprostol; "IGF+ASA+MP" represents cultures treated with 150 ng/ml IGF-1, 250 μg/ml ASA and 80 ng/ml misoprostol simultaneously.

IGF-1 (150 ng/ml) stimulated GAG synthesis by 78%, but ASA showed no significant effect on this stimulation (FIG. 5). This observation would suggest that the stimulatory effect of IGF-1 may not be through a prostaglandin synthetic pathway, since ASA did not affect IGF-1-dependent stimulation. Also, the individual stimulatory effects on GAG synthesis of IGF-1 and misoprostol (when these agents were added to the cultures separately) were 93% greater than the stimulatory effect of the combined treatment (FIG. 6). However, the use of IGF-1 in combination with a prostaglandin and TGF-β is nonetheless warranted in view of these results.

What is claimed is:

1. A pharmaceutical composition comprising a prostaglandin having the structure:

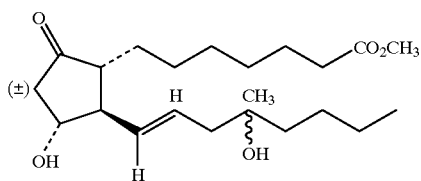

and TGF-β, wherein the prostaglandin and TGF-β are present in an amount effective to stimulate production of chondrocyte matrix.

2. The pharmaceutical composition of claim 1 further comprising IGF-1, wherein the prostaglandin, TGF-β and IGF-1 are present in an amount effective to stimulate production of chondrocyte matrix.

3. A method for treating a subject which comprises administering to the subject a pharmaceutical composition of claim 1 in an amount effective to stimulate production of chondrocyte matrix.

4. The method of claim 3 wherein the pharmaceutical composition further comprises IGF-1, wherein the prostaglandin, TGF-β and IGF-1 are present in an amount effective to stimulate the production of chondrocyte matrix.

5. A method for treating a subject which comprises administering to the subject, in combination, (a) a pharmaceutical composition comprising a prostaglandin having the structure:

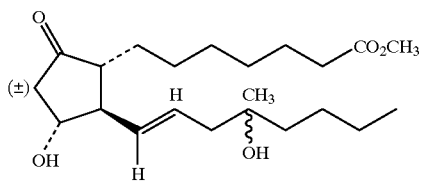

and (b) a pharmaceutical composition comprising TGF-β; wherein the prostaglandin and TGF-β are administered in an amount effective to collectively stimulate the production of chondrocyte matrix.

6. A method for treating a subject which comprises administering to the subject in combination, (a) a pharmaceutical composition comprising a prostaglandin having the structure:

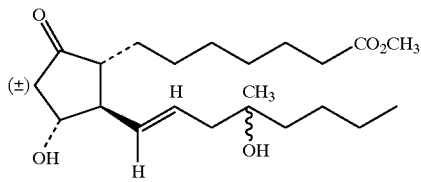

(b) a pharmaceutical composition comprising TGF-β and (c) a pharmaceutical composition comprising IGF-1; wherein the prostaglandin, TGF-β and IGF-1 are administered in an amount effective to collectively stimulate production of chondrocyte matrix.

7. The method of claim 5 wherein the subject is being treated for damage to chondrocyte matrix caused by non-steroidal anti-inflammatory therapy.

8. The method of claim 6 wherein the subject is being treated for damage to chondrocyte matrix caused by non-steroidal anti-inflammatory therapy.

9. The method of claim 5 wherein the subject is being treated for damage to chondrocyte matrix due caused by IL-1 therapy.

10. The method of claim 6 wherein the subject is being treated for damage to chondrocyte matrix caused by IL-1 therapy.

11. A method for treating a subject which comprises administering to the subject a pharmaceutical composition of claim 2 in an amount effective to stimulate production of chondrocyte matrix.

* * * * *